(12) United States Patent
McAuley et al.

(10) Patent No.: US 7,856,981 B2
(45) Date of Patent: Dec. 28, 2010

(54) NASAL POSITIVE PRESSURE DEVICE

(75) Inventors: Alastair Edwin McAuley, Auckland (NZ); Nicholas Charles Alan Smith, Hamilton (NZ); Dominic Robert Doyle, London (GB)

(73) Assignee: Fisher & Paykel Healthcare Limited (NZ)

( * ) Notice: Subject to any disclaimer, the term of this patent is extended or adjusted under 35 U.S.C. 154(b) by 994 days.

(21) Appl. No.: 10/495,092

(22) PCT Filed: Nov. 12, 2002

(86) PCT No.: PCT/NZ02/00246

§ 371 (c)(1), (2), (4) Date: Mar. 2, 2005

(87) PCT Pub. No.: WO03/041780

PCT Pub. Date: May 22, 2003

(65) Prior Publication Data

US 2005/0166927 A1   Aug. 4, 2005

(30) Foreign Application Priority Data

Nov. 16, 2001   (NZ) .................................... 515549

(51) Int. Cl.
*A61M 15/00* (2006.01)
*A61M 15/08* (2006.01)
*A62B 7/00* (2006.01)
*A61G 10/00* (2006.01)

(52) U.S. Cl. ........................ 128/207.13; 128/203.17; 128/204.18; 128/204.24; 128/204.25; 128/205.26; 128/206.11; 128/207.18

(58) Field of Classification Search ............ 128/203.17, 128/204.18, 204.24, 204.25, 205.26, 206.11, 128/207.18

See application file for complete search history.

(56) References Cited

U.S. PATENT DOCUMENTS

| 3,682,171 | A | * | 8/1972 | Dali et al. ............... 128/207.18 |
| 5,097,827 | A | | 3/1992 | Izumi |
| 5,148,802 | A | | 9/1992 | Sanders et al. |
| 5,245,995 | A | | 9/1993 | Sullivan et al. |
| 5,477,852 | A | | 12/1995 | Landis |

(Continued)

FOREIGN PATENT DOCUMENTS

WO   WO 8703704   6/1987

*Primary Examiner*—Patricia M Bianco
*Assistant Examiner*—Nihir Patel
(74) *Attorney, Agent, or Firm*—Knobbe, Martens, Olson & Bear LLP

(57) ABSTRACT

The present invention is related a nasal positive airway pressure device. The nasal device utilizes an engagement means located about nasal cannulae to engage and secure the cannulae within the nares of a patient. The engagement means is a nasal scaling flap. The flap in its natural bias is tapered, the wide-open end of which is shaped to conform to the facial contours of a patient's nose around the outside of the nose. Thus in a closed form, the flap provides a cup-like device that is fitted around the patient's nose and prevent the nasal device from falling from the patients nose. In the open form, which allows for placement and fitting of the nasal device, the flap is intended to be in a bent back position to aid insertion of the nasal cannulae into the patient's nares.

10 Claims, 9 Drawing Sheets

U.S. PATENT DOCUMENTS

| | | |
|---|---|---|
| 5,513,635 A | 5/1996 | Bedi |
| 5,533,506 A | 7/1996 | Wood |
| 5,735,272 A * | 4/1998 | Dillon et al. ........... 128/207.18 |
| 5,752,510 A | 5/1998 | Goldstein |
| 6,093,169 A * | 7/2000 | Cardoso .................. 604/94.01 |
| 6,321,923 B1 | 11/2001 | Wood |
| 6,354,293 B1 * | 3/2002 | Madison ................ 128/204.13 |

* cited by examiner

NASAL POSITIVE PRESSURE DEVICE

BACKGROUND TO THE INVENTION

1. Field of the Invention

The present invention relates to apparatus for treating sleep apnoea. More specifically, the present invention provides a nasal positive airway pressure device which is reliable and comfortable to wear and, consequently, more acceptable to the patient.

2. Summary of the Prior Art

Obstructive Sleep Apnoea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The procedure for administering CPAP treatment has been well documented in both the technical and patent literature. Briefly stated, CPAP treatment acts as a pneumatic splint of the airway by the provision of a positive pressure, usually in the range 4 to 20 cm $H_2O$. The air is supplied to the airway by a motor driven blower whose outlet passes via an air delivery hose to a nose (or nose and/or mouth) mask sealingly engaged to a patient's face by means of a harness or other headgear. An exhaust port is provided in the delivery tube proximate to the mask. More sophisticated forms of positive airway pressure devices, such as bi-level devices and auto-titrating devices, are described in U.S. Pat. No. 5,148,802 of Respironics, Inc. and U.S. Pat. No. 5,245,995 of Rescare Limited, respectively.

U.S. Pat. No. 5,477,852 of Airways Ltd, Inc. discloses a nasal positive airway pressure device that has a pair of nasal members each having a cannula tip to be inserted into the nares of the patient. Each cannula is tapered from a substantially circular cross-section outside the patient's nostril to a substantially oval cross-section at the tip inserted into the nostril. An inflatable cuff surrounds each cannula with the interior space of the cuff communicating with the lumen of the cannula through at least one aperture in the sidewall of the cannula. The nasal members are connected to one or more flexible hoses that, in turn, are connected to a source of positive air pressure. In use, positive air pressure is supplied to each cannula tip through the air hoses and nasal members. The positive air pressure inflates the cuffs to hold the nasal members in place and to effect treatment. The nasal device of U.S. Pat. No. 5,477,852 are attached to headgear that is located about a patient's head, this headgear could be considered by many patient's as cumbersome and uncomfortable.

Conventional nasal masks used for administrating CPAP treatment are also considered uncomfortable and cumbersome, also prior art nasal masks and the like are noisy (due to air leaks). These disadvantages in many cases are a formidable obstacle to patient acceptance of such treatment. Therefore, a substantial number of patients either cannot tolerate treatment or choose to forego treatment. It is believed a substantial number of such patients could benefit from a nasal positive airway pressure apparatus that is more convenient to use and comfortable to wear, thereby resulting in increased treatment compliance.

SUMMARY OF THE INVENTION

It is an object of the present invention to attempt to provide a nasal positive pressure device which goes some way to overcoming the abovementioned disadvantages in the prior art or which will at least provide the industry with a useful choice.

In a first aspect the present invention consists in a device for delivering a supply of gases to a patient comprising or including:

a nasal member having a pair of nasal cannulae extending from the distal end of said nasal member, transportation means adapted to be connected to the proximal end of said nasal member, engaging means located about said nasal cannulae that are adapted in use to provide engagement and securement of said nasal cannulae within said nares of said patient, and a retaining or compressive force about the nose of said patient.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings.

DETAILED DESCRIPTION OF THE PREFERRED EMBODIMENTS

It will be appreciated that the improvements to nasal plugs as described in the preferred embodiments of the present invention can be used in respiratory care generally or with a ventilator, but will now be described below with reference to their use in a humidified Continuous Positive Airway Pressure (CPAP) system.

CPAP System

Figure 1:
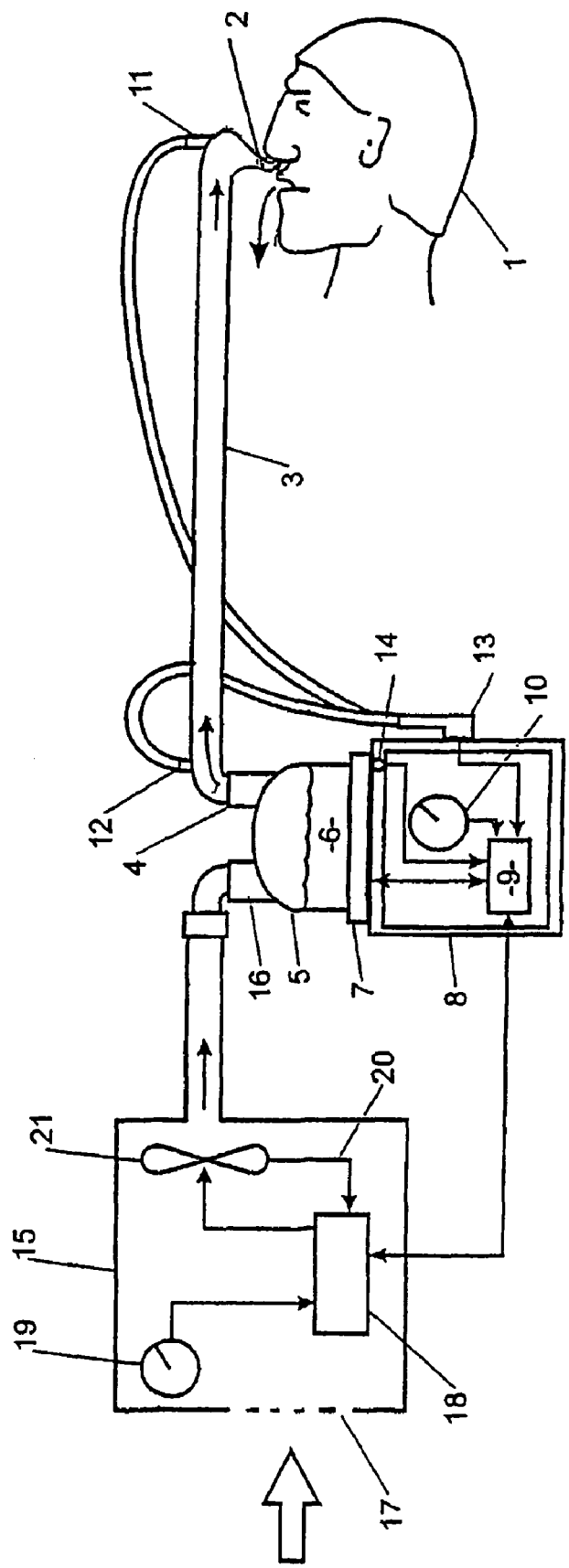
FIG. 1 is a block diagram of a humidified continuous positive airway pressure system as might be used in conjunction with the present invention.

With reference to FIG. 1 a CPAP system is shown in which a patient 1 is receiving humidified and pressurised gases through the nasal device 2, such as nasal cannulae, that are connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 that contains a volume of water 6. Inspiratory conduit 3 may contain heating means or heater wires (not shown) that heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient are exhausted to the ambient surroundings.

Blower 15 is provided with variable pressure regulating means or variable speed fan 21 that draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Plugs

In a general form, the nasal device 2 generally consists of Y-shaped connector piece that connects the nasal device to the breathing circuit, transportation passageway or conduit 3, which is connected to the source of pressurised gas. Each arm of the Y-shaped connector is connected to a nasal tube, which are each connected to nasal members. The nasal members have a tapered end terminating in an aperture (cannula), the tapered end has disposed about it nasal plugs. In use, when a patient inserts each of the nasal plugs into their nasal cavities and positive pressure ventilation therapy is commenced, pressurised gases pass through the conduit 3, into the Y-shaped connector, through each of the nasal tubes exiting into the patient's nostrils through each nasal cannula, thereby administering positive pressure ventilation therapy to the patient.

Figure 2:
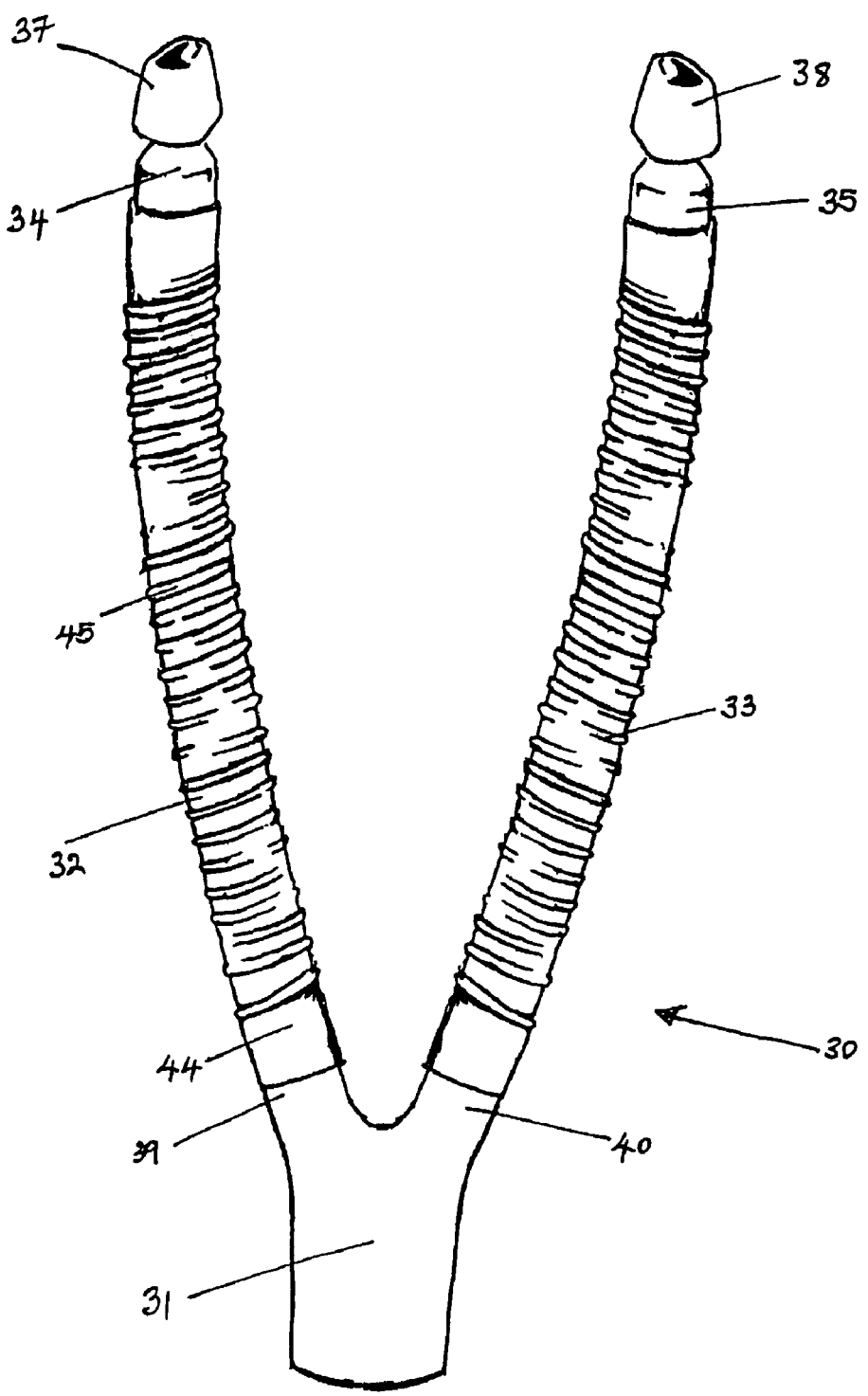
FIG. 2 is a front view of the nasal plugs and associated tubing of one embodiment of the present invention, where the nasal plugs are made from a foam type material.
Figure 4:
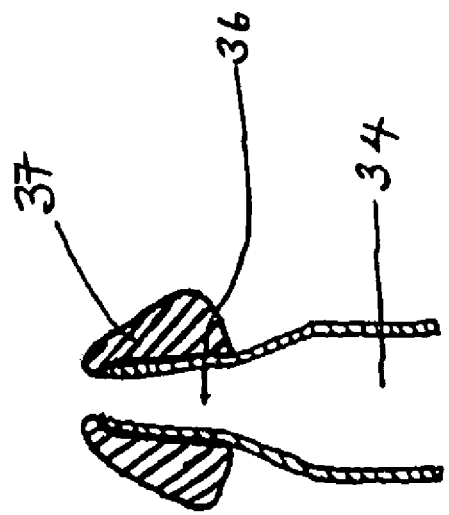
FIG. 4 is a cross-sectional view of a nasal plug of FIG. 2 through AA as shown in FIG. 3.
Figure 3:
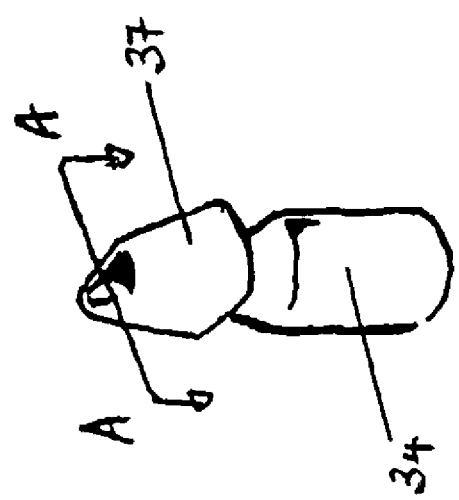
FIG. 3 is a close-up front view of the two nasal plugs of FIG. 2.

Referring to FIGS. 2 to 4, there is shown a nasal positive airway pressure device 30 in accordance with a first embodiment of the present invention. Device 30 consists of a Y-shaped connector piece 31 (that is connected to the gases outlet end of the conduit 3), and a pair of nasal tubes 32, 33 each terminating in a nasal member 34, 35. The Y-shaped connector 31 and each of the nasal members 34, 35 are hollow cylinders or tubes that allow for the flow of gases therein. The nasal members terminate in an aperture that is the outlet of pressurised gases from the ventilation system into the patient's nasal cavities. The end of each nasal member 34, 35 defines a cannula, which is basically a tapered end 36 terminating in an aperture. Fitted about each cannula 36 is a nasal plug 37, 38 configured and dimensioned to fit within the nasal cavities of a patient. In the first form of the present invention the nasal plugs 37 and 38 are made of a foam type material, preferably a closed-cell foam that has been moulded into the shape of a nostril, that shape being a generally frustoconical.

The Y-connector 31 and nasal members 34, 35 are each moulded from a polycarbonate type material, although other substantially rigid materials may be used, such as rigid plastics or metal. Suitable plastics include homopolymers, copolymers, blends and mixtures of polystyrene, ABS, polycarbonate, acrylics, or polyethylene. Suitable metals include stainless steel, titanium, aluminium and alloys thereof. One end of each nasal tube 32, 33 is fitted over the arms 39, 40 of the Y-connector 31 and the other end of each nasal tube 32, 33 is adapted to be connected to each nasal member 34, 35, for example the nasal member may be fitted within the nasal tubes 32, 33. These fittings may be of any convenient manner suitable for coupling without substantial loss of gas pressure, such as by friction fit, snap fit, gluing, welding, threading or the like. The foam nasal plugs 37, 38 are fixed about the cannulae 36 by appropriate fixing means, for example by gluing, in a manner that preserves gas pressure.

The nasal tubing 32, 33 are conduits 44 that is, in the preferred form, molded from an elastomeric material such as a Polyethylene/EVA mixture or silicon rubber. The conduit preferably has a "ribbed" "or corrugated" construction to allow bending, (the ribs are referenced as 45). This conduit construction may be accomplished by blowing the molten elastomeric material to form an endless cylinder that is forced outwards against the internal surface of a rotating mould that impresses the ribs onto the conduit. The conduit 44 may also have within it a helically wound heater wire (not shown) that preferably sits against or adjacent to the internal wall of the conduit along its length. The purpose of having a conduit with a heater wire is to reduce the condensation of the gases within the conduit. The nasal tubing 32, 33 being a "ribbed" conduit provides the advantage of being able to be easily manipulated by the patient for additional patient comfort.

In use, the patient need only apply pressure to the sides of the foam nasal plugs 37, 38 thereby depressing the foam deforming the shape of each of the nasal plugs so that each is easily insertable into each nasal cavity. Once each plug is within each cavity the foam will expand to its original form where the external surface of the foam abuts the internal surface of the patient's nasal cavity, thereby filling the area within each nostril. The foam nasal plug provides a seal between the cavity and the cannula, effectively eliminating gases leakage, as the expanding foam provides an outward force upon the inner surface of each of the patient's nasal cavities, which also prevents each plug from falling from the nasal cavity.

Nasal members 34, 35 have disposed in them at least one, but preferably a number of, small holes (not shown) that act as vents to exhaust the gases that are exhaled by the patient. The holes and thus the nasal members may be covered with an appropriate type of material that acts as a diffuser.

Figure 6:
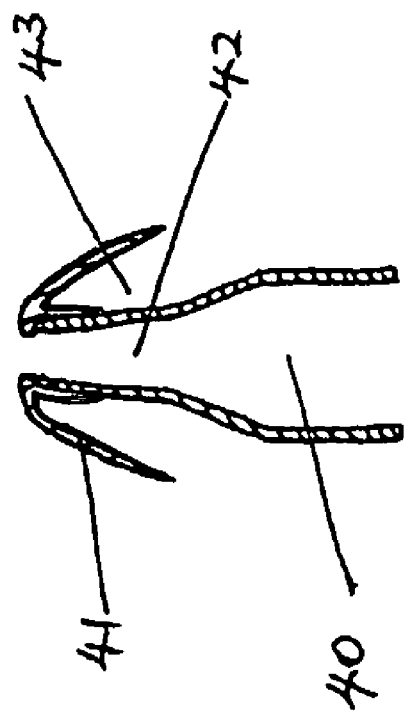
FIG. 6 is a cross-sectional view of the nasal plug through BB as shown in FIG. 5.
Figure 5:
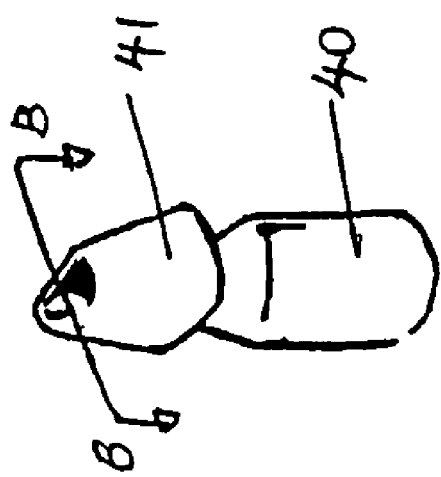
FIG. 5 is a front view of one of two nasal plugs of a further embodiment of the present invention, where the nasal plugs are made from a silicon type material.

In a further form of the nasal device of the present invention, the nasal plugs may be constructed from a silicon type material. With reference to FIGS. 5 and 6, the nasal device in this form is almost identical to that as shown in FIG. 2, the difference being the nasal plugs are manufactured from a silicon type material that is formed in an inverted U-shape. The nasal plug and nasal member, as shown in FIG. 6, is a cross-section through BB of FIG. 5. The silicon nasal plug 41 is adapted to be connected to the tapered end 42 of the respective nasal member 40. This connection may be provided by any appropriate means as discussed earlier in relation to the embodiment of the nasal plugs, but more preferably by a type of glue.

Again, to allow for exhaust and diffusion of exhaled gases from the patient each of the nasal members (of which only one, labelled 40, is shown in FIGS. 5 and 6 have disposed in them at least one, but preferably a number of, small holes (not shown) that act as vents to exhaust the gases that are exhaled by the patient into the ambient air. The holes and thus the nasal members may be covered with an appropriate type of material that acts as a diffuser.

The nasal plug 41 may be made from other appropriately flexible materials that will be deformed under a pressure applied by the user of the nasal device. In use, as a patient inserts the U-shaped plugs into his or her nares the arms of each of the U-shaped plugs are compressed, effectively reducing the space 43 between the tapered end 42 and the interior surface of the nasal plug 41. Once the plugs are completely inside the nares, the arms of each U-shaped plug expand to their natural position, causing the plugs to be retained within the nares by way of friction.

In both of the abovementioned forms the nasal plugs provide a good seal within the patient's nasal cavities, thereby reducing the effects of gases leakage. As the nasal plugs are deformable, they are easily fitted by the patient and provide greater patient comfort when in use. In addition, the forces of the expanding materials, once inserted, hold the nasal plugs within the nasal cavities in a manner that is more comfortable to the patient than prior treatment devices.

Inflatable Cuffs

Figure 7:
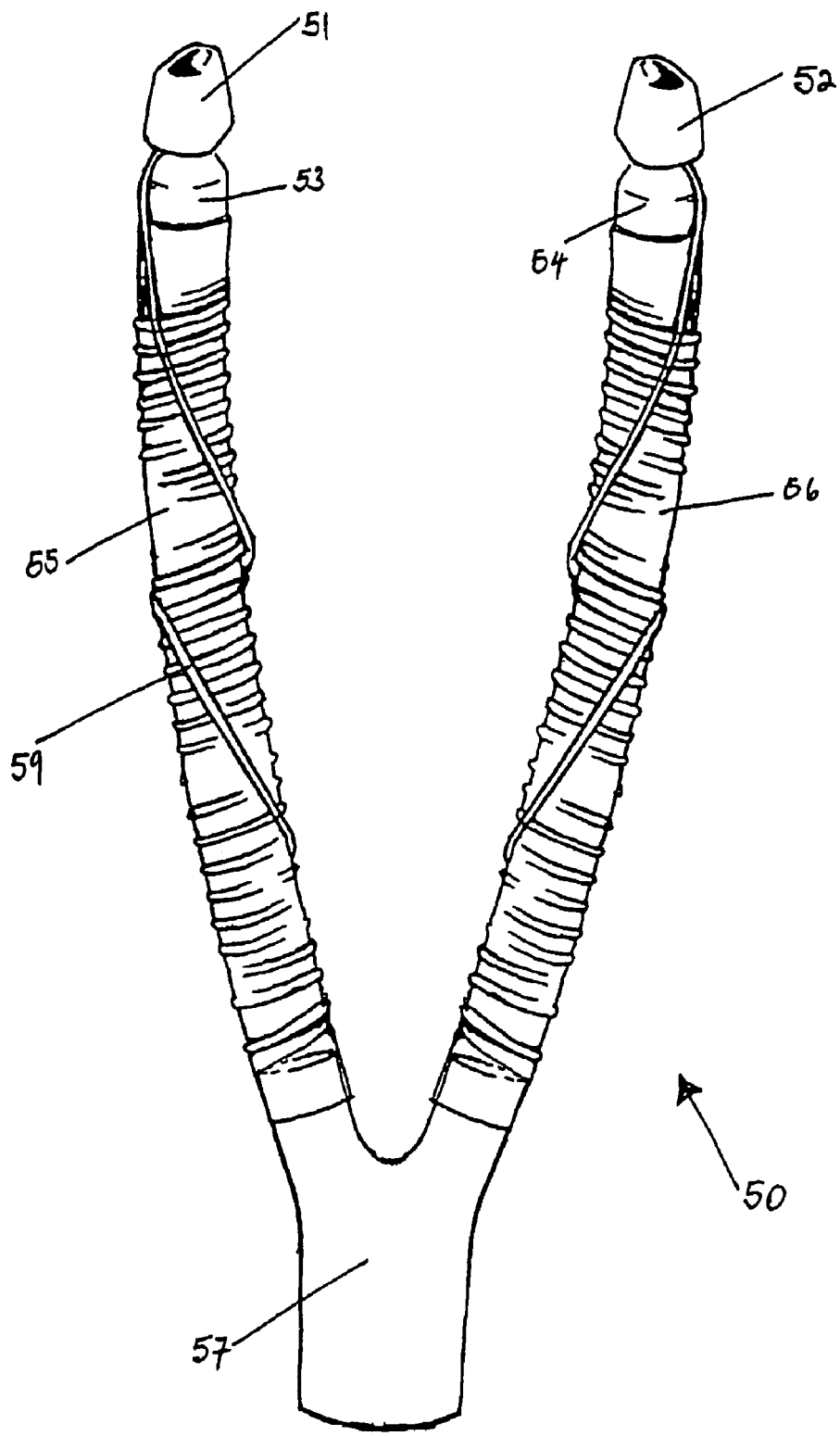
FIG. 7 is a front view of the nasal plugs and associated tubing of yet another embodiment of the present invention, where the nasal plugs are inflatable cuffs.
Figure 9:
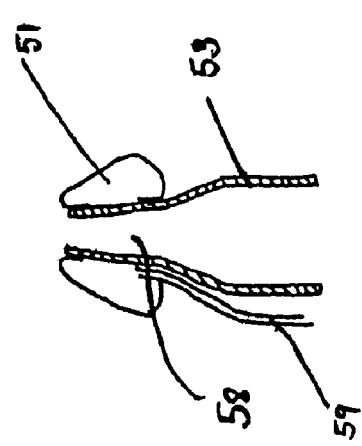
FIG. 9 is a cross-sectional view of the inflatable cuff, through CC as shown in FIG. 8, when the cuff is in the inflated condition.
Figure 8:
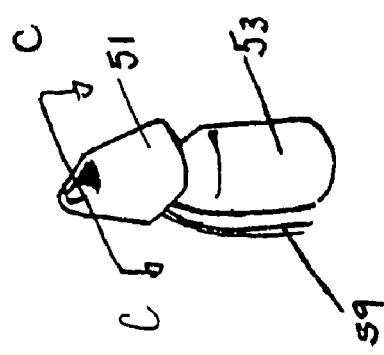
FIG. 8 is a front view of one the inflatable cuffs of FIG. 7.

In accordance with a further embodiment of the present invention, FIGS. 7 to 9 show a nasal device 50 that utilises inflatable cuffs 51, 52. The cuffs are attached by appropriate means, for example by moulding or gluing or the like, to the nasal members 53, 54. The nasal members 53, 54 are adapted to be connected to nasal tubes 55, 56 and the nasal tubes to the Y-connector as described above.

Figure 10:
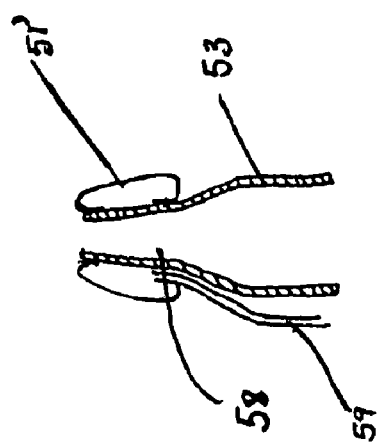
FIG. 10 is a cross-sectional view of the inflatable cuff, through CC as shown in FIG. 8, when the cuff is in the deflated condition.

Each inflatable cuff 51, 52 surrounds the tapered end 58 (see FIG. 8) and provides a force, when in use, within the nasal cavity, to hold the tapered end 58 in position within the patient's nares in a manner to be explained below. Each tapered end 58 of the nasal members 53, 54 are preferably substantially oval or elliptical in cross-section at the open end that is distal to nasal members 53, 54, and gradually tapers to a substantially circular cross-section outside the patient's nares. The inflatable cuffs 51, 52 surrounding each tapered end 58 are made of a plastics material, and a small inflation tube 59, 60, made from a flexible plastics material communicates with the interior space of each cuff, preferably through the cuff wall. Both inflation tubes 59, 60 are connected to an inflation device, where when the inflation device provides gases to the tubes (59, 60) the cuffs are inflated with the gases. FIG. 9 shows one such inflatable cuff 51 in cross-section when the cuff is inflated in an "in use" form, whereas FIG. 10 shows one such cuff 51' in cross-section when the cuff is the deflated "insertion" form.

The inflation device that could be used to provide gases to the inflation tubes may be a non-return valve with a fitting at one end, in which a plastic syringe (without the needle) could be placed. The syringe can then be used to force air into each of the cuffs. When the syringe is removed the non-return valve would keep the air in the cuffs. This is similar to the inflation system on an ET tube. To deflate the cuff, the syringe can be inserted into the inflating tubes and valve and draw the gases from the cuff.

Alternatively, a further inflation device is anticipated which is a small pump mechanism. This would involve having a plastic gases holding compartment with two non-return valves attached on either side of the compartment. One valve would allow air to pass into the compartment from the atmosphere, and once the compartment is compressed, for example, by the patient's fingers, gases are forced through the second non-return valve, into the inflating tubes, inflating the cuffs. To deflate the cuffs, the pump mechanism would be supplied with a bleed valve, which is preferably hand operated.

In use, when the patient wishes to commence positive pressure ventilation therapy, he or she must place each cuff within his or her nasal cavities and start the inflation device. As air flows through the inflation tubes 59, 60 the cuffs 51, 52 will inflate and provide a force against the internal walls of the nasal cavities, preventing the cuffs from falling from the cavities. Again, this embodiment of the nasal plugs of the present invention has the advantage of providing the patient with a comfortable alternative to prior art nasal devices.

Nasal Snap Flap

Figure 13:
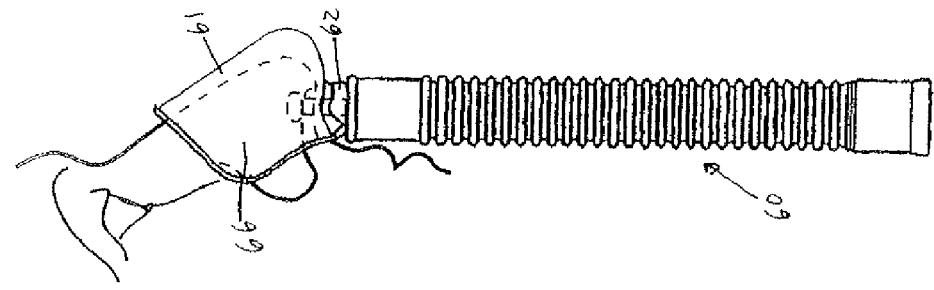
FIG. 13 is a side elevational view of the nasal flap, nasal plugs and associated tubing of FIG. 11, where the nasal flap is in the in use, closed position, and showing the patient.
Figure 12:
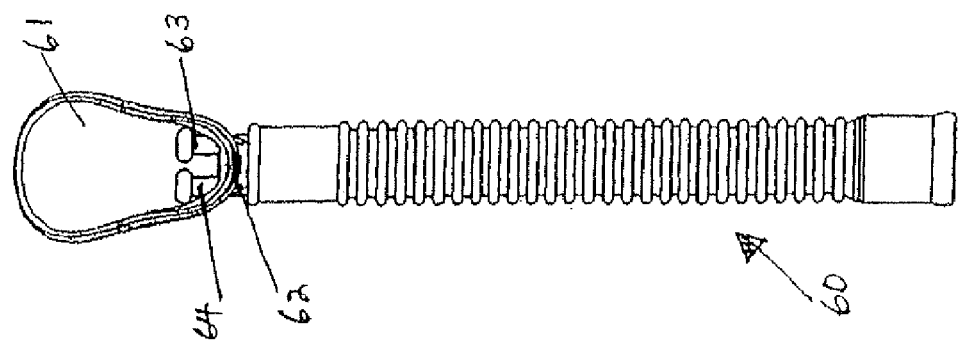
FIG. 12 is a front view of the nasal flap, nasal plugs and associated tubing of FIG. 11, where the nasal flap is in the in use, closed position.
Figure 11:
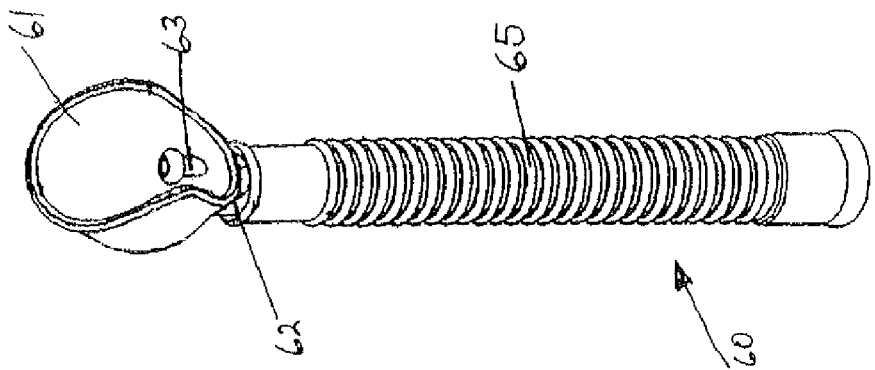
FIG. 11 is a perspective view of the nasal flap, nasal plugs and associated tubing of still a further embodiment of the present invention, where the nasal flap is in the in use, closed position.
Figures 14, 15, 16:
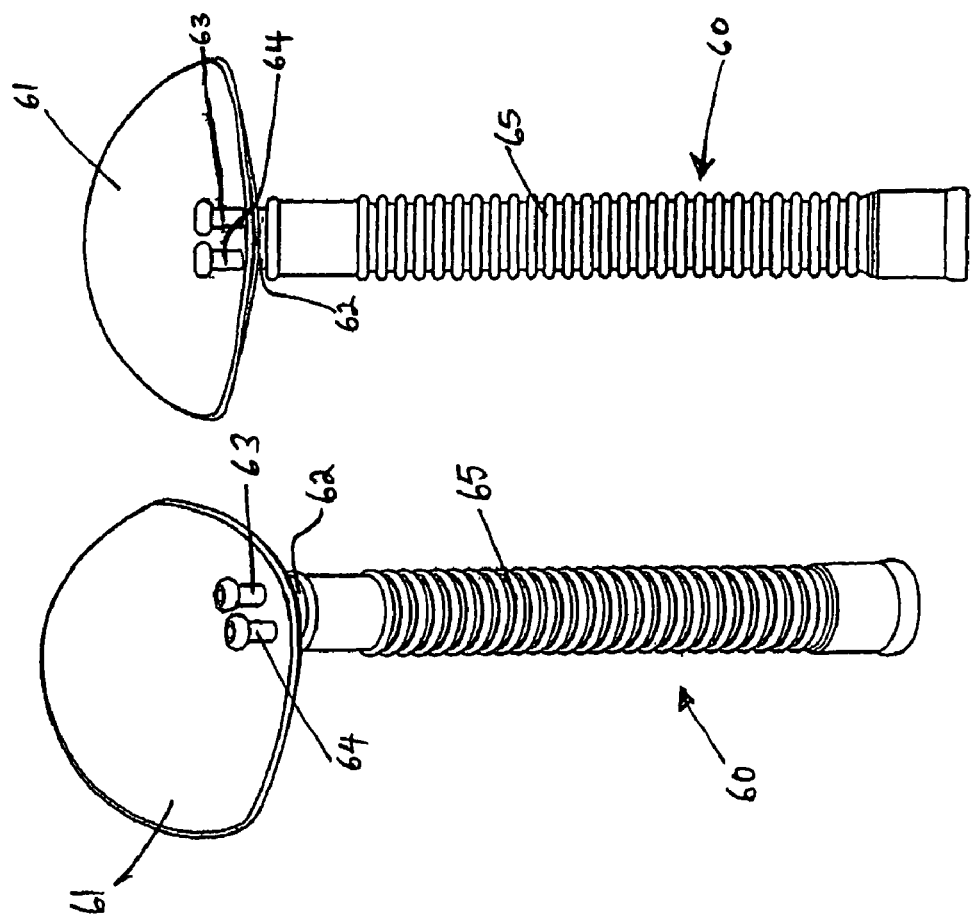
FIG. 14 is a perspective view of the nasal flap, nasal plugs and associated tubing of FIG. 11, where the nasal flap is in the open position.
FIG. 15 is a front view of the nasal flap and nasal plugs of FIG. 11, where the nasal flap is in the open position.
FIG. 16 is a side view of the nasal flap and nasal plugs of the forth form of the present invention, where the nasal flap is in the open position.
Figure 17:
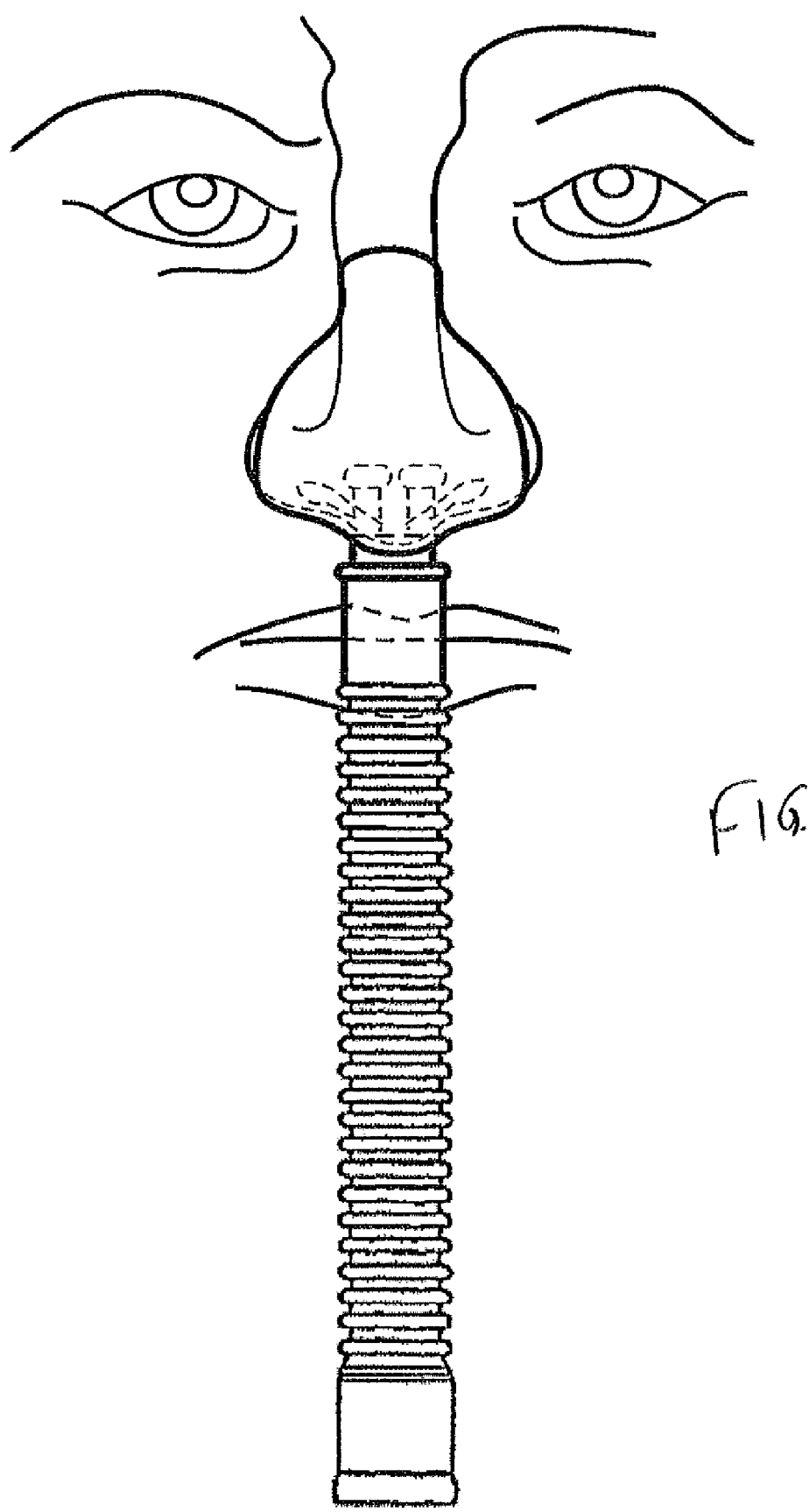
FIG. 17 is a front elevational view of the nasal flap, nasal plugs and associated tubing of FIG. 11, where the nasal flap is in the in use, closed position, and showing the patient.

In accordance with a fourth form of the present invention, FIGS. 11 to 16 show a nasal device 60 that utilises an engagement means located about nasal cannulae to engage and secure the cannulae within the nares of a patient. The engagement means is a nasal sealing flap 61. The flap 61 in its natural bias is tapered, the wide-open end of which is shaped to conform to the facial contours of a patient's nose around the outside of the nose. Thus in a closed form, as shown in FIGS. 11 to 13, the flap provides a cup-like device that is fitted around the patient's nose and prevent the nasal device 60 from falling from the patients nose. In the open form, that allows for placement and fitting of the nasal device 60, the flap 61 is intended to be in a bent back position, as shown in FIGS. 14 to 16, to aid insertion of the nasal cannulae 63, 64 into the patient's nares.

The nasal device comprises the nasal sealing flap 61 connected by appropriate means to a nasal member 62 that terminates in at least one nasal cannula, although in the preferred form two cannulae 63, 64 are provided, one for each of the patient's nares. The flap 61 and cannulae 63, 64 may be integrally formed or the flap 61 may be attached about the cannulae 63, 64 (by appropriate means, such as gluing) after the cannulae have been formed. Furthermore, the cannulae 63, 64, flap 61 and nasal member 62 may all be integrally formed by injection moulding or the like methods. The cannulae 63, 64 extend through the proximate end of the flap 61, so that in use, upon placing the flap about the patient's nose the cannulae extend into the nasal cavities of the patient's nose. The other end of the nasal member 62 is connected, again by appropriate fixing means, such as by friction fit, snap fit, gluing, welding, threading or the like, to a nasal tube 65.

The nasal tube 65 is a conduit that is, in the preferred form, moulded from an elastomeric material such as a Polyethylene/EVA mixture or silicon rubber. The conduit preferably has a "ribbed" "or corrugated" construction to allow bending that is constructed as described above with relation to the tubing 32, 33 of FIG. 2. The nasal tube 65 is preferably connected to the inspiratory conduit 3 and thus to the rest of the ventilation system as detailed with reference to FIG. 1 above. In an alternative form the nasal tube 65 and conduit 3 may be one tube.

In use, to attach the nasal device to the nose and nares, the patient bends back the flap 61 to the open position, as shown in FIGS. 14 to 16, and inserts the nasal cannulae 63, 64 into each nostril. To enable the retaining of the cannulae 63, 64 within the nares the flap 61 is bent into the closed position, the flap 61 providing a cup-like seal around the patient's nose. The flap is bent back into the open position to enable removal from the patient, by simply pressing on its outer periphery 66, until it snaps into the bent back position, in which it will stay unaided. The flap 61 may be adjusted into its operational position by pressing on its outer periphery 66 until it snaps forward to press against the outside of the nose.

It will be appreciated that the flap provides enough compressive force on the nose to keep the nasal device and conduit in place without the need for straps. This allows the administering of positive airway pressure ventilation therapy to be considerably less obtrusive than traditional methods. Additionally, the flap may provide a substantially airtight seal about the patient's nose.

In all forms of the nasal device as discussed above, the friction between the plugs or cuff of the device and the interior surface of the patient's nares prevents the plugs or cuffs from falling from the patient's nares. Although it is appreciated that headgear could be used to ensure securement of the nasal device to the patient. Thus, the device may be secured to the head of the user with headgear (not shown) by attaching straps of the headgear at an appropriate point along the length of each nasal tube or at the nasal members. Furthermore, a clip or the like could be used to attach the tubing associated with the nasal device to the patient's clothes.

We claim:

1. A device for use as part of a system for delivering a supply of gases to a patient comprising:
    a nasal member in fluid communication with a pair of nasal cannulae, said nasal member adapted to receive breathing gases and direct said gases to said nasal cannulae,
    a securing flap arranged about said nasal cannulae and adjustable between a first biased position and a second biased position,
    in said first biased position, said flap is arranged in an open curve adjusted away from said nasal cannulae, permitting said nasal cannulae to be inserted or removed from the nares of said patient,
    in said second biased position, said flap conforms to a cup-like shape, substantially conforming to, and engaging with the bridge of said patient's nose, said engagement providing a compressive force about said patient's nose and securing said nasal cannulae in the nares of said patient.

2. A device according to claim 1 wherein one end of said nasal member is adapted to connect to a flexible conduit.

3. A device according to claim 2 wherein said nasal member is a tubular member defining a further passage for the flow of gases from said flexible conduit to the nares of said patient.

4. A device according to claim 1 wherein said nasal member is integrally formed with said flap.

5. A device according to claim 4 wherein said nasal cannulae are also formed integrally with said flap.

6. A device as claimed in any one of claims 1, 2, 3, 4 and 5 wherein in said first biased position said securing flap is arranged in an open configuration with peripheral portions of said securing flap deflected outwardly, the open configuration permitting the nasal cannulae to be inserted within and removed from the nares of the patient without said securing flap interfering with the patient's nose, and in said second biased position said securing flap is arranged in a closed configuration with said peripheral portions deflected inwardly, said securing flap substantially conforming to the bridge of the patient's nose in the closed configuration and providing said compressive force.

7. A device as claimed in claim 6 wherein said securing flap will remain in either said first or second biased position unaided, said securing flap elastically adjustable between said first and second biased positions, substantial movement of said securing flap from said first biased position toward said second biased position causing the securing flap to bias to the second biased position and assume a predefined shape,
    said securing flap is adjusted between said biased positions by applying a force to peripheral portions of the securing flap in a direction of the desired biased position,
    said securing flap moving through a transition region between the first and second biased positions, the securing flap biasing to the second biased position after moving past the transition region.

8. A device as claimed in claim 7 wherein said securing flap is arranged around said nasal cannulae, the open configuration permitting the nasal cannulae to be inserted within and removed from a patient's nares, the closed configuration conforming to an exterior contour of a patient's nose and providing said compressive force.

9. A device for use as part of a system for delivering a supply of gases to a patient comprising:
    a nasal member in fluid communication with a pair of nasal cannulae, said nasal member adapted to receive breathing gases and direct said gases to said nasal cannulae,
    a securing flap arranged about said nasal cannulae and adjustable between a first biased position and a second biased position, said securing flap being adjusted between said first and second biased positions by applying a forced to peripheral portions of the securing flap in a direction of the desired biased position, said securing flap remaining in said first biased position and said second biased position unaided, in said first biased position said securing flap is arranged in an open configuration, with peripheral portions of said securing flap deflected outwardly in an open curve away from said nasal cannulae to permit said nasal cannulae to be inserted or removed from the nares of said patient, in said second biased position said flap is arranged in a closed configuration with said peripheral portions deflected inwardly to form a cup-like shape so that said flap substantially conforms to, and engages with, the bridge of said patient's nose, said engagement providing a compressive force about said patient's nose that secures said nasal cannulae in the nares of said patient, wherein said securing flap is elastically adjustable between said first and second biased positions, substantial movement of said securing flap from said first biased position toward said second biased position causing the securing flap to pass through a transition region and bias to the second biased position and assume a predefined shape.

10. A device for use as part of a system for delivering a supply of gases to a patient comprising:

a nasal member in fluid communication with a pair of nasal cannulae, said nasal member adapted to receive breathing gases and direct said gases to said nasal cannulae, a securing flap arranged about said nasal cannulae and adjustable between a first biased position and a second biased position, in said first biased position, said flap adjusted away from said nasal cannulae, permitting said nasal cannulae to be inserted or removed from the nares of said patient, in said second biased position, said flap substantially conforming to, and engaging with the bridge of said patient's nose, said engagement providing a compressive force about said patient's nose and securing said nasal cannulae in the nares of said patient, wherein in said first biased position said securing flap is arranged in an open configuration with peripheral portions of said securing flap deflected outwardly, the open configuration permitting the nasal cannulae to be inserted within and removed from the nares of the patient without said securing flap interfering with the patient's nose, in said second biased position said securing flap is arranged in a closed configuration with said peripheral portions deflected inwardly, said securing flap substantially conforming to the bridge of the patient's nose in the closed configuration and providing said compressive force, wherein said securing flap will remain in said first biased position and said second biased position unaided, said securing flap elastically adjustable between said first and second biased positions, substantial movement of said securing flap from said first biased position toward said second biased position causing the securing flap to bias to the second biased position and assume a predefined shape, said securing flap is adjusted between said biased positions by applying a forced to peripheral portions of the securing flap in a direction of the desired biased position, said securing flap moving through a transition region between the first and second biased positions, the securing flap biasing to the second biased position after moving past the transition region, and wherein in the first biased position the securing flap is arranged in an open curve, and in the second biased position the securing flap conforms to a cup-like shape.

* * * * *